(12) United States Patent
Soller

(10) Patent No.: US 6,766,188 B2
(45) Date of Patent: Jul. 20, 2004

(54) TISSUE OXYGEN MEASUREMENT SYSTEM

(75) Inventor: Babs R. Soller, Northboro, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/269,826

(22) Filed: Oct. 11, 2002

(65) Prior Publication Data

US 2003/0088163 A1 May 8, 2003

Related U.S. Application Data

(60) Provisional application No. 60/329,406, filed on Oct. 15, 2001.

(51) Int. Cl.[7] ................................................. A61B 5/00
(52) U.S. Cl. ........................ 600/477; 600/475; 600/326; 600/364
(58) Field of Search ................................ 600/476, 473, 600/477, 326, 364, 475

(56) References Cited

U.S. PATENT DOCUMENTS

| 5,355,880 A | * | 10/1994 | Thomas et al. ............. 600/326 |
| 5,435,309 A | * | 7/1995 | Thomas et al. ............. 600/310 |
| 5,515,864 A | | 5/1996 | Zuckerman |
| 5,593,899 A | | 1/1997 | Wilson et al. |
| 5,813,403 A | | 9/1998 | Soller et al. |
| 5,879,294 A | | 3/1999 | Anderson et al. |
| 5,931,799 A | | 8/1999 | Guastella et al. |
| 6,015,969 A | | 1/2000 | Nathel et al. |
| 6,124,597 A | | 9/2000 | Shehada et al. |
| 6,216,021 B1 | | 4/2001 | Franceschini et al. |

OTHER PUBLICATIONS

Cingo et al., "Multivariate Calibration Modeling of Liver Oxygen Saturation Using Near–Infrared Spectroscopy" *Biomedical Diagnostic* 3911: 230–236 (2000).
Soller et al., "Simultaneous Measurement of Hepatic Tissue pH, Venous Oxygen Saturation and Hemoglobin by Near Infrared Spectroscopy" *Shock* 15: 106–111 (2001).
Soller et al., "Application of Fiberoptic Sensors for the Study of Hepatic Dysoxia in Swine Hemorrhagic Shock" *Crit. Care Med* 29: 1438–1444 (2001).

* cited by examiner

*Primary Examiner*—Eleni Mantis Mercader
(74) *Attorney, Agent, or Firm*—Fish & Richardson P.C.

(57) ABSTRACT

A device and method in accordance with the invention for determining the oxygen partial pressure ($PO_2$) of a tissue by irradiating the tissue with optical radiation such that the light is emitted from the tissue, and by collecting the reflected or transmitted light from the tissue to form an optical spectrum. A spectral processor determines the $PO_2$ level in tissue by processing this spectrum with a previously-constructed spectral calibration model. The tissue may, for example, be disposed underneath a covering tissue, such as skin, of a patient, and the tissue illuminated and light collected through the skin. Alternatively, direct tissue illumination and collection may be effected with a hand-held or endoscopic probe. A preferred system also determines pH from the same spectrum, and the processor may determine critical conditions and issue warnings based on parameter values.

24 Claims, 3 Drawing Sheets

Tissue $PO_2$ during the four phases of the study. Baseline (normotensive & normothermic), CPB-cold (hypotensive & hypothermic), CPB-warm (hypotensive & normothermic), CPB+6 (normotensive & normothermic). * $p < 0.05$ compared to baseline.

TISSUE OXYGEN MEASUREMENT SYSTEM

CROSS-REFERENCE TO RELATED APPLICATIONS

This application is based on U.S. provisional application No. 60/329,406, entitled "Tissue Oxygen Measurement System," filed on Oct. 15, 2001, of which priority is claimed.

STATEMENT REGARDING FEDERALLY SPONSORED RESEARCH

This invention was made with government support under National Space Biomedical Research Institute contract no. NCC9-58-226 under NASA Cooperative Agreement NCC9-58; the government of the United States of America may have certain rights in the invention.

FIELD OF THE INVENTION

The present invention relates generally to medical devices for use in assessing reduced oxygen delivery to regional tissue beds. Specifically, the invention relates to devices and methods for measuring tissue oxygenation either alone or in combination with other parameters such as pH, by using optical reflectance spectrum of the tissue.

BACKGROUND

Tissue levels of oxygen are an important indicator of the metabolic status of cells. If tissue oxygen falls below cellular demands, then cells perish. Organs, particularly those with high metabolic rates, are especially susceptible to incurring irreversible damage when oxygen is inadequate. It has previously been shown that tissue pH is a useful indicator of anaerobic metabolism, and as such can indicate cells at risk. However, tissue oxygen levels change prior to a drop in pH, so that detection of a low oxygen level could provide an earlier indication of a potential problem. Measurement of tissue oxygenation could also provide a useful early measure to assess the degree of success in restoring oxygen to oxygen-deficient tissue.

Cellular processes are complex, and beyond the question of whether oxygen is transported to the cells in sufficient quantity, one may ask whether the cells are able to use the available oxygen. The combination of a tissue pH measurement and a tissue oxygen measurement would be useful in determining whether a given tissue bed can actually utilize oxygen which is delivered. In a recent paper, applicant has shown that the simultaneous measurement of tissue pH and oxygenation can be used to indicate the onset of dysoxia (defined as the mismatch between oxygen demand and supply). Soller et al., "Application of fiberoptic sensors for the study of hepatic dysoxia in swine hemorrhagic shock," Crit. Care Med, 29:1438–1444 (2001). The detection of the onset of dysoxia in this manner may therefore permit earlier or more effective preventive interventions in humans. However, the technology for measuring these parameters is at present limited.

Solving this need would be a major contribution to clinical practice. Clinically, oxygen levels can change as a result of many causes: bleeding, trauma, poor cardiac performance, low blood pressure and impaired circulation, among others. Diabetic patients often have compromised tissue perfusion, particularly in their legs and feet. This may result in ulcers and ultimately require amputation. For management of such a chronic condition, it would be especially desirable to possess a technique or sensor for dependably monitoring tissue oxygenation.

Tissue oxygenation is traditionally determined through the measurement of the partial pressure of oxygen ($PO_2$) present in the cells or the interstitial fluid. Typically, tissue $PO_2$ is measured by inserting an invasive $PO_2$ sensor (such as an electrode-based sensor or a dye-coated fiber optic sensor) into the tissue that is to be monitored.

Ideally, it would be advantageous if this measurement could be made spectroscopically, such that the measurement process is non-invasive and does not physically penetrate or stress the tissue. A number of researchers have investigated spectroscopic methods to determine tissue oxygenation. In doing so, they have typically relied upon quantifying some related parameter. For example, some researchers have considered the spectroscopic measurement of arterial or venous blood oxygen to constitute a suitable measure of tissue oxygenation. Arterial blood levels do not, however, respond rapidly to regional changes in reduced oxygen, so this indicator may fail to reflect prevailing tissue oxygenation at a site of interest. Local or regional measurement of venous oxygen saturation, on the other hand, is a satisfactory measure of tissue oxygenation, since local venous blood is collected blood returning from the local tissue. Hutchinson Technology of Hutchinson, Minn. has an existing product which measures venous hemoglobin oxygen saturation in tissue, such as muscle tissues, at depths up to several inches using near infrared (NIR) light. The technology is described, for example, in U.S. Pat. No. 5,879,294 and possibly other patents, and also in promotional material or research publications of that group. Another company, Somonetics, sells a NIR device which measures a combination of venous and arterial oxygen saturation in the brain. A large number of issued patents are also directed to various optical methods of measuring blood and tissue levels of oxygenated hemoglobin or oxygen saturation. These include, for example, U.S. Pat. Nos. 5,515,864, 5,593,899, 5,931,799, 6,015,969, 6,123,597, and 6,216,021. Dr. Britton Chance at the University of Pennsylvania has also patented a number of inventions in this area.

In general, known devices and methods for evaluating the level of oxygen have tended to rely on secondary or related measurements, or upon relatively invasive sensors or slower assays.

It would therefore be desirable to have a system that determines tissue $PO_2$ directly and non-invasively in a local tissue region.

SUMMARY OF THE INVENTION

A device in accordance with one aspect of the invention determines the oxygen partial pressure ($PO_2$) of a tissue, which may, for example, be disposed underneath a covering tissue, such as skin, of a patient, or which may be directly contacted or imaged by the device. The device includes a light source for irradiating the tissue with optical radiation such that the light is reflected from the tissue, and also includes a probe for collecting the reflected light to form a reflection spectrum. The device further includes a spectral processor that determines the $PO_2$ level in tissue by processing this spectrum and a mathematical model relating optical properties to $PO_2$ of the tissue.

A method of the invention includes the step of first illuminating the tissue with optical radiation to irradiate the underlying tissue, and collecting a reflection spectrum from the illuminated tissue. The method also includes the step of determining tissue $PO_2$ by processing the collected spectrum with a mathematical model relating optical properties to $PO_2$ of the tissue.

The invention also includes a spectral calibration model for tissue $PO_2$. The model is constructed from a previously compiled calibration data set comprised of direct $PO_2$ measurements and a set of spectral samples collected in coordination with the measurements.

By "tissue", as used herein, is meant any tissue or organ present, e.g., in a patient. This definition encompasses any collection of cells, e.g., epithelial cells, muscle cells, skin cells, or any specific organ, e.g., the heart, kidney, or liver, in the patient. The optical radiation preferably is visible and near infrared radiation or includes a substantial range of near infrared radiation. The radiation may be between about 400 and about 2500 nm, and preferably, the radiation is between 450 and 1100 nm.

The mathematical model of the invention is constructed prior to processing a collected spectrum by first compiling a calibration data set. The calibration data set is formed by collecting multiple optical spectra from a representative tissue sample of a subject, and also measuring the tissue $PO_2$ value simultaneously (e.g., by conventional means). Preferably such data sets are collected from multiple subjects and over a wide range of $PO_2$ values. The optical spectra and known $PO_2$ values are then processed with a mathematical multivariate calibration algorithm, such as a partial least-squares (PLS) fitting algorithm described below, to determine a model, e.g. a formula or calibration equation, relating $PO_2$ to the spectral values collected from the sample. In constructing the model, other parameters, such as pH, temperature and the like may also be measured and fitted to the model, and these subject pH, temperature or other parameters may also be measured at run time for enhanced accuracy. In another embodiment, one or more parameters such as pH, temperature or the like may be varied during acquisition of the calibration data set, serving to enhance the variety of conditions covered by the model, and hence, its accuracy, without becoming explicit variables in the calibration formula so produced.

Once determined, the model is stored, e.g., in the memory of a computer, and then used to transform the optical spectrum obtained from a patient into a $PO_2$ value for the underlying sample tissue. Most preferably, the model used in the analysis step is determined once and is applicable to a wide variety of patients. In this case, the model is preferably robust enough to account for features such as skin color, fat content, weight, etc., which vary from one patient to the next. Alternatively, a range of models can be generated. In this case, during a procedure, the model suitable for a particular patient is selected and is then used to determine the tissue $PO_2$ from spectra acquired from that patient. In yet a different embodiment, a special calibration formula may developed to correct for a specific spectral contribution (e.g., the contribution of skin scattering and coloration in spectra from individuals of diverse ethnicity), and this special calibration formula may be used to pre-process or normalize the spectrum obtained from a given patient prior to applying the $PO_2$ calibration equation. Suitable procedures for effecting such spectral correction are described in commonly-owned U.S. patent application Ser. no. 10/086,917, filed on Feb. 28, 2002, and which is hereby incorporated by reference in its entirety.

The calibration model is a synthetic construct, and is previously and independently constructed by a procedure of first collecting a calibration set comprising a plurality of reflected or transmitted light samples from tissue, and also a plurality of direct $PO_2$ reference measurements from the same tissue, where the light samples and reference measurements are taken in an extended data collection protocol during which the tissue $PO_2$ and other conditions vary over a wide range. The calibration model is then constructed from the calibration set, and is subsequently applied to the spectrum collected from the local region in the tissue of interest. In this manner, tissue $PO_2$, which itself has no "spectrum", is accurately and quickly detected by processing light non-invasively collected at the surface of the local region of tissue.

It is known that a related parameter (e.g., venous oxygen saturation) may be spectrally measured, for example, by the methods reported by Cingo et al. in Proc SPIE, 3911:230–236, (2000) or by Soller et al. in Shock, 15:106–111, (2001), or other known assay, and that venous oxygen saturation is linearly related to tissue $PO_2$ in the range between about 15% and about 80% saturation. Since a number of spectrally significant contributors to oxygenated and deoxygenated hemoglobin, as measured by venous oxygen saturation, are present in the tissue and contribute to the tissue spectrum, the present invention has discovered that by applying a multivariate fitting algorithm to local $PO_2$ measurements and local tissue spectra, it might be possible to develop a "virtual model" of $PO_2$. During the initial calibration model development, the reference $PO_2$ measurements, may, for example, be taken by an invasive tissue $PO_2$ sensor placed directly in the target tissue or organ. Similarly, the spectrum may be collected from the same tissue site. The model so developed will then accurately represent $PO_2$ itself, rather than a few closely related but potentially divergent factors.

The set of spectral and direct measurements for defining the calibration model are preferably collected as the $PO_2$ level (and other parameters) are varied over an extended range. In a proof-of principle example to construct a calibration equation or model for spectral measurement of tissue $PO_2$, tissue reflectance spectra and raw data measurements are taken every thirty seconds from the muscle of a patient's palm as the patient undergoes a cardiopulmonary bypass (CPB) procedure. The CPB procedure introduces great changes in pH, mean arterial blood pressure and $PO_2$ over the course of more than an hour for each subject, before the patient's heart is stopped, the subject is placed on the heart-lung machine and cooled, and the subject is subsequently re-warmed and revived. Data is preferably collected from diabetic and non-diabetic patients, to introduce further range or additional variation in the tissue response data.

The resulting data set with multiple embedded parameter variations is then processed to develop a calibration model for determining tissue $PO_2$ from the collected reflectance spectra returned from the underlying muscle. This model, that is to be later applied to independently-collected spectra from arbitrary subjects, is determined prior to taking a run time reflectance or transmittance spectrum by collecting multiple optical spectra, each occurring at known $PO_2$ values, from a representative sample. The optical spectra and known $PO_2$ values are then processed with a mathematical multivariate calibration algorithm, such as a partial least-squares (PLS) fitting algorithm, to derive the calibration model. The model may feature a linear or non-linear mathematical equation relating actual level of $PO_2$ to a reflection or absorption spectrum taken from the sample. Once constructed or verified, the model is applied to independently-gathered spectra to quantify tissue $PO_2$ directly, non-invasively and in real time.

Thus, the invention provides an optical method for determining the oxygen partial pressure in a tissue. The target tissue may, for example, be disposed underneath a covering tissue (for example, muscle tissue illuminated through the overlying skin), or may be directly accessed by the optical probe (for example, cardiac tissue having an exposed surface and accessed during open chest or minimally-invasive surgery by a fiber optic surface contact probe, or by a focused illuminator/collector probe).

BRIEF DESCRIPTION OF THE DRAWINGS

These and other features and advantages of the invention will be understood from the description herein and claims appended hereto, taken together with illustrative figures, wherein:

DETAILED DESCRIPTION OF THE INVENTION

The present invention provides a method that determines the partial pressure of oxygen ($PO_2$) in a region of a subject's tissue by collecting a sample of reflected or transmitted light from the tissue and then processing the sample with a series of computational steps. The sample is a spectral sample, with light spanning a number of frequencies (or, equivalently, wavelengths), and is detected such that the spectrum may be represented numerically, e.g., as a row vector with entries corresponding to the intensity value for each of a number of sub-intervals of the spectral band. The spectrum is processed by applying a mathematical model that relates distribution of values in the spectrum to the actual level of tissue $PO_2$. The general technique of deriving a calibration equation or model for assay of a material having a defined reflectance spectrum but presented in a confounding background such as tissue is described in numerous papers, including those previously cited, in U.S. Pat. No. 5,813,403 by Soller, and elsewhere. A specific derivation will be described further below for tissue oxygen partial pressure. Of particular note is the discovery that by constructing a "virtual" model for the spectrum of the partial pressure of free oxygen present in tissue, one may directly measure $PO_2$ by simply applying the model to a non-invasively collected light sample (technically, tissue $PO_2$ is a condition that affects many contributing factors, rather than being a substance having a distinct spectrum).

The virtual $PO_2$ model, or calibration equation, is constructed prior to collecting and processing the optical spectrum of a local region of tissue in which $PO_2$ is to be measured. The model can be constructed, as described in greater detail below, by taking a series of spectra from tissue samples having known and widely ranging $PO_2$ values, and then processing the spectra and the $PO_2$ values with a partial least squares (PLS) fitting algorithm. Once so constructed, this virtual $PO_2$ model is applied to determine $PO_2$ from a collected tissue spectrum, e.g., comparing the spectrum to the model.

Figure 1:
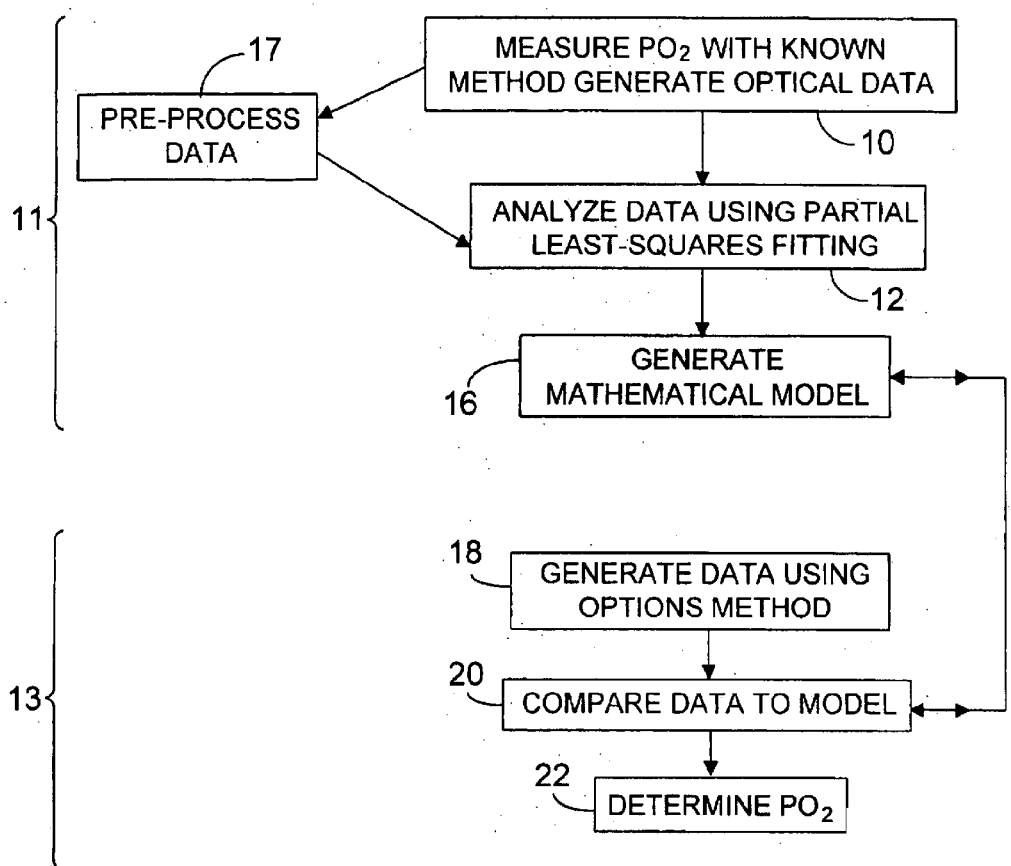
FIG. 1 is a flow chart showing the steps used for $PO_2$ measurement according to the method of the invention.

An overall procedure for effecting a spectral measurement in accordance with the invention is shown in FIG. 1, a flow chart illustrating process steps effective to determine the tissue $PO_2$ of a sample. A model of tissue $PO_2$ is first generated with a series of steps indicated generally by the bracket 11 in FIG. 1, and the model is stored, e.g., in a computer memory. The model is then accessed later in time and used in combination with a second series of steps, indicated generally by the bracket 13, to determine the oxygen partial pressure in tissue at the sampled region.

To construct the model, optical data (reflectance spectra) are collected from the sample and $PO_2$ is concurrently measured with a known reference sensor (step 10). During the collection process, the level of $PO_2$ varies over a great range, so that the collected data set represents spectra and $PO_2$ readings over that range. In a prototype implementation discussed further in the EXAMPLE below, the reference sensor can be a 0.5 mm reference sensor distributed by Diametrics Medical, Inc., that measures three parameters: pH, $PO_2$, and temperature. In the study discussed in detail below, reference $PO_2$ and pH sensors were placed directly in a muscle, the abductor digiti minimi (V). A separate, near infrared spectroscopic (NIRS) fiber optic probe (such as the optical fiber spectral probe of the aforesaid '403 patent) was placed over the hypothenar eminence (palm muscle) to collect light returned from the same palm muscle. Data were collected every 30 seconds during the course of a surgery and for 6 hours following CPB to acquire a set of spectra, each with a corresponding $PO_2$ measurement, as the $PO_2$ varied over an extended range of values. In general, one may arrange for the $PO_2$ to be varied using any known technique, such as by constricting a vessel or otherwise adjusting the blood flow to the sampled region of the patient's tissue. In the prototype construction, such variation was arranged by collecting the data during a major surgery, a cardiopulmonary bypass operation, in which the various surgical steps—placing the subject on a heart-lung machine, stopping patient's heart, and subsequently re-warming and reviving the patient—induced changes in $PO_2$ over a range from low or even zero to normal values, over the course of several hours. Because the $PO_2$ of a muscle (or other) sample may exhibit a spatial dependence, the reflectance spectrum was collected from an area of the tissue in close proximity to the reference sensors.

In the prototype procedure for collecting a spectral/measurement calibration data set from which the model was to be constructed, 18 elective cardiac surgical subjects were each sampled during a respective CPB surgery.

Continuing with a discussion of FIG. 1, the data collected at stage 10 may be preprocessed or may be collected in various ways in a stage 17 to enhance its information content. The data set is then processed at stage 12 with a numerical algorithm to construct a calibration equation or model. Preprocessing may include filtering using known smoothing algorithms to improve their signal-to-noise ratio, for instance, when data contains large amounts of noise. Preprocessing may also include removing spectral factors related to human subject variability, such as skin color as discussed in U.S. patent application Ser. No. 10/086,917 previously cited, and which is hereby incorporated by reference. A technique such as mean-centering may also be applied in a pre-processing stage prior to processing with the numerical algorithm. In this case, x-y arrays corresponding to different $PO_2$ values are averaged together to generate an average x-y array; the average x-y array is then subtracted from each individual x-y array taken at different $PO_2$ values using Equation 1 below:

$$\hat{y}_{ik} = y_{ik} - y_{i,ave}$$

where the "hat" over $y_{ik}$ indicates the data point is normalized by the mean-centering operation. Other pre-processing routines may be useful, such as taking a first or second derivative of the spectra prior to processing, or making multiplicative scatter corrections to the spectra (see, e.g., H. Martens and T. Naes, "Multivariable Calibration", J. Wiley & Sons (1989)).

Thus, for example, multiple samples may be taken and averaged at each point, and/or a reflector phantom may be positioned on the tissue to provide a reference spectrum used to normalize the collected tissue reflectance spectra. Also, both actual $PO_2$ measurements and optical measurements can be recorded from multiple localized areas, with values averaged together to increase the robustness or accuracy of the data.

The actual (conventionally-measured) $PO_2$ reading of the sample, and parameters such as the temperature and pH, if measured, are each recorded as a single numerical value, while the reflection spectrum is in the form of an x-y array of points. The x values of the array represent particular optical wavelengths or frequencies, while they values represent reflectance intensities corresponding to these wavelengths or frequencies. An absorption spectrum can be determined from the reflection spectrum. In that case, a reference spectrum is taken by placing the spectral illuminator/collector in contact with standard reflector, such as a 50% Spectralon Reference Standard (Labsphere Corp.) and measuring the reflected light. The absorption spectrum $A(\lambda)$ can be calculated by taking the log of the reference spectrum $I_b(\lambda)$ divided by the reflection spectrum $I_r(\lambda)$, following Equation 2 below:

$$A(\lambda)=\log [I_b(\lambda)/I_r(\lambda)]$$

Spectra for the model can be taken from tissue lying underneath a patient's skin or other tissue, or may be collected directly from the tissue surface if it is exposed tissue. In both cases, visible and near infrared optical wavelengths are preferably used to measure the spectra. These wavelengths are particularly advantageous in the former case as they undergo minimal attenuation by the intervening skin layer.

Following pre-processing, a PLS algorithm is used to process the x-y arrays and corresponding $PO_2$ values (step 12) to generate a mathematical model. PLS algorithms are well-known for statistical analysis of x-y arrays of data points. Other multivariate calibration algorithms, such as least-squares fitting, neural networks, and principal components regression, can also be used to generate the model. These algorithms are described in Thomas, "A Primer to Multivariate Calibration", Analytical Chemistry, 66: 795–804 (1994). Processing the input data can be achieved using a computer and a commercially available software package incorporating the PLS algorithm. For instance, the Grams/32 software package (Galactic Industries, Inc.) can be used to perform the PLS analysis. Alternatively, a similar PLS algorithm can be coded directly into the computer. Such an algorithm is defined, for example, in "Numerical Recipes Example Book (C)", supra. The salient features of the algorithm are described below. A complete guide to the operation of the Grams/32 software is described in detail in the user's manual corresponding to the software package.

The PLS fitting algorithm performs a statistical analysis on the input x-y arrays and known $PO_2$ values to determine a model relating absorbance spectra to the sample's $PO_2$. The algorithm is based on a quantitative spectral decomposition technique that simultaneously decomposes and regresses the $PO_2$ data and the spectral data. To ascertain their relationship, the PLS algorithm performs a statistical regressive analysis of the relationship between the absorption spectra in the form of the x-y arrays of data points and the $PO_2$ of the sample. Based in part on this regressive analysis, the PLS algorithm generates a mathematical model (step 16) with regression coefficients that are optimized to best fit the input data. The algorithm may also generate other statistical information, as discussed in the aforesaid '403 patent, indicating the quality and accuracy of the model. It should be noted that when the given tissue conditions suggest that a non-linear relationship exists, then a different multivariate fitting procedure may be employed to enhance the accuracy of the model.

In a qualitative sense, the PLS algorithm determines $PO_2$-induced changes in the reflection spectra and correlates these to the $PO_2$ value. For example, chemical species such as myoglobin and hemoglobin contained in tissue samples have absorption properties which are $PO_2$-dependent; as the $PO_2$ changes, the absorption spectra of the tissue also changes. The PLS algorithm interprets changes in each x-y array induced by $PO_2$, and generates a mathematical equation relating the absorption spectra to the predicted $PO_2$ of the tissue.

The numerical model is made as robust as possible. In general, this is accomplished by taking a large number of spectra at different $PO_2$ values and under different experimental conditions. The spectra and $PO_2$ values are then processed using the PLS algorithm as described above. Most preferably, the model is sensitive only to $PO_2$-induced changes in the absorbance of the tissue, and is not affected by the presence of skin. Thus, when the tissue is not exposed with a surgical procedure, reflectivity measurements are made at known $PO_2$ values using near infrared wavelengths which are not strongly absorbed by the skin. In this way, scattering processes in the skin, which are not indicative of the underlying tissue's reflectance properties, are not included in the measured spectra. The model thus does not have to account for skin type, e.g., color, thickness, and optical quality, and other properties related to the skin which have a large degree of patient-to-patient variation. However, when wavelengths in the visible portion of the spectrum are to be used, corrections for these patient-to-patient variations may be required.

In addition, the model is preferably not sensitive to parameters associated with the optical measurement, such as the distance between the optical measuring device and the sample, or slight changes in the optical power. When not employing a tissue-contacting probe, the effect of these factors is minimized by taking, during step 10, a variety of reflection spectra and corresponding $PO_2$ measurements using a variety of experimental conditions. Moreover, the accuracy of the model is increased by taking measurements at a variety of sample temperatures. Measurements taken at known values of $PO_2$ with patients having different degrees of fat content, skin roughness and color, height, weight, blood type, and other characteristics can be analyzed and included in the model to increase its accuracy.

Preferably, a single, robust model which is invariant to different patients is determined prior to the optical $PO_2$ measurement. Alternatively, a range of different models can be determined and stored in the memory of a computer for later use. In this case, the appropriate model is selected according to the patient and used with optical spectra measured from the patient to determine $PO_2$. Different models, for example, can correspond to patients having different temperatures, skin color, fat content, medical problem, etc. As a particular example, temperature can be independently determined by a temperature sensor, e.g., a thermocouple or optical pyrometer, and then analyzed to select different models that are effective for different temperature ranges.

In addition, reflection or transmission spectra and $PO_2$ measurements for the model can be taken from in vitro solutions composed of chemical species typically found in tissue, e.g., water, myoglobin, hemoglobin. Such solutions have the advantage that their properties can be easily changed in a controlled manner, thereby allowing a large number of measurements to be taken under slightly different conditions. The accuracy of the model can be further increased using statistical methods, such as cross-validation. In general, cross-validation is an algorithm used in combination with PLS to obtain an objective assessment of the magnitude of prediction errors resulting from the model and to determine the optimal number of factors for the model. The cross-validation algorithm is included in the Grams/32 software package.

The software package also singles out "outlier" x-y arrays which can decrease the accuracy of the model. Outlier arrays are erroneous data due to non-standard measurement conditions, such as the presence of fingerprints on the sample holder or a large drop in optical power. These data typically have dramatically different properties compared to data measured under more conventional measurement conditions, and thus decrease the accuracy of the $PO_2$ determination if included in the model. Similarly, outlier $PO_2$ measurements due to experimental deviations in the reference $PO_2$ measurements should not be used to calculate the model.

Optical data are taken from the sample (step 18) using the optical $PO_2$-measuring device described below to determine the $PO_2$ once the model is established and stored in a computer's memory.

The device may be the same as that used to measure data for the model, but calibration transfer procedures, known to those skilled in the art, can be used to employ the model on new devices. As described above, data are in the form of an x-y array of points, where y typically indicates the absorption of the optical measurement, e.g., the reflectivity, as a function of the frequency or wavelength. Measurements from the sample are then multiplied with the PLS regression coefficients derived from the mathematical model (step 20) to determine the $PO_2$ (step 22). Alternatively, the data are multiplied by the PLS regression coefficients of the previously determined model to determine the $PO_2$.

By "tissue", as used herein, is meant any tissue or organ of a patient. This definition encompasses any collection of cells, e.g., epithelial cells, muscle cells, skin cells, or any specific organ, e.g., the heart, kidney, or liver, in the patient. The optical radiation is preferably near infrared (NIR) radiation, or extends from the visible into the NIR. Most preferably, the radiation is between about 450 nm and about 1100 nm, where it is understood the region 450–1100 nm encompasses the visible and part of the near infrared spectral region, while 400–700 nm is considered visible light. This band includes wavelengths that undergo minimal interference from water absorption in the skin and other tissue, thereby enhancing the penetration depth of the radiation, and it includes a number of wavelengths that are affected by the phenomena of interest.

EXAMPLE

A near infrared spectroscopic (NIRS) fiber optic probe was placed over the hypothenar eminence in 6 diabetic and 12 normal (non-diabetic) elective cardiac surgical patients to collect light reflected from the same muscle. Reference $PO_2$ and pH sensors were inserted in the abductor digiti minimi (V) nearby. Table 1 below represents the patient characteristics for the 18 subjects of the study.

TABLE 1

| Patient Characteristics (N = 18) | | |
|---|---|---|
| Age | Average | 65.5 ± 2.1 |
| Gender | Male/Female | 14/4 |
| Operation | CABG/Valve/CABG + Valve | 8/5/5 |
| Diabetes | Yes/No | 6/12 |

Data were collected every 30 seconds during surgery and for 6 hours following CPB while blood pressure was lowered as a result of the surgery. Calibration equations were developed from one third of the data collected using partial least squares regression. These calibration equations were used along with the remaining two-thirds of the spectral data to investigate sensitivity of the NIRS measurement to physiologic changes resulting from CPB. NIRS and reference pH and $PO_2$ measurements were compared using the root mean squared deviation (RMSD). As represented by Table 2 below, NIRS pH and $PO_2$ at baseline were compared to values during CPB just before rewarming commenced (low blood pressure, low temperature), after rewarming (low blood pressure, normal temperature) just before discontinuation of CPB, and at 6 hours following CPB (normal blood temperature and blood pressure) using mixed model ANOVA.

Figure 2:
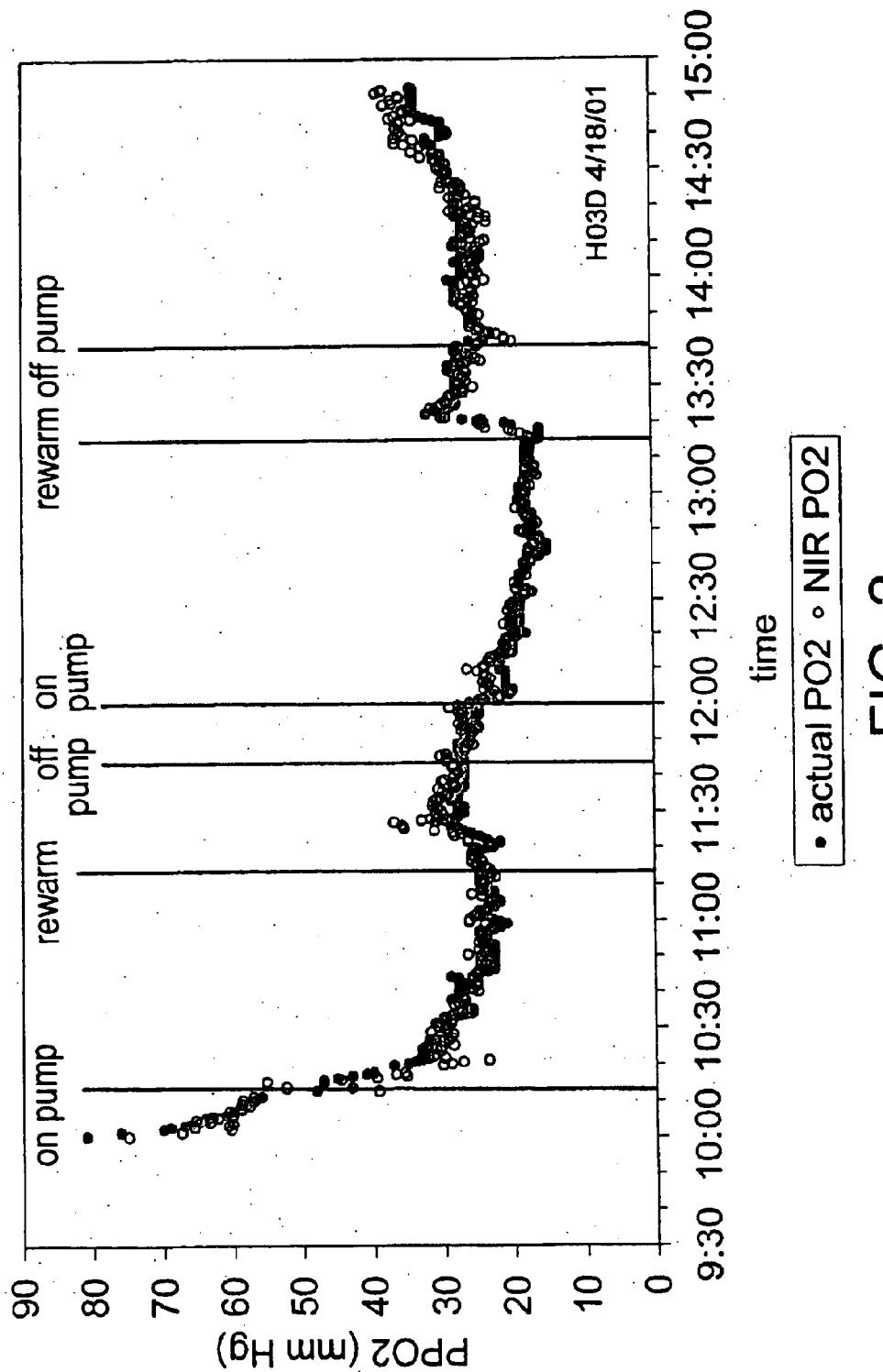
FIG. 2 is a comparison chart showing $PO_2$ determined by direct sensor measurement and determined by the method of the present invention.

For the 18 patients, NIRS pH and $PO_2$ were well correlated with the invasive measurement of pH ($R^2=0.84$) and $PO_2$ ($R^2=0.66$) with an average RMSD of 0.022±0.008 pH units and 6±3 mmHg, respectively. The agreement between NIRS non-invasive $PO_2$ and the invasive measurement is illustrated in FIG. 2 for one of the patients during the course of his surgery, where closed circles indicate the invasive measurement of $PO_2$ and open circles represent the spectroscopic, non-invasive measurement. In FIG. 2, the non-invasive (calculated) values $PO_2$ were made according to the present invention, and the invasive (measured) $PO_2$ data points were determined by a known probe. Changes in $PO_2$ resulting from surgical procedures such as being placed on the heart-lung machine (on pump) and in warming the patient back to normal body temperature are clearly visible in the course of the several-hour procedure. As illustrated in FIG. 2, the calibration equation or "virtual" model of tissue $PO_2$ accurately predicted the values measured by conventional invasive probe technology.

Figure 3:
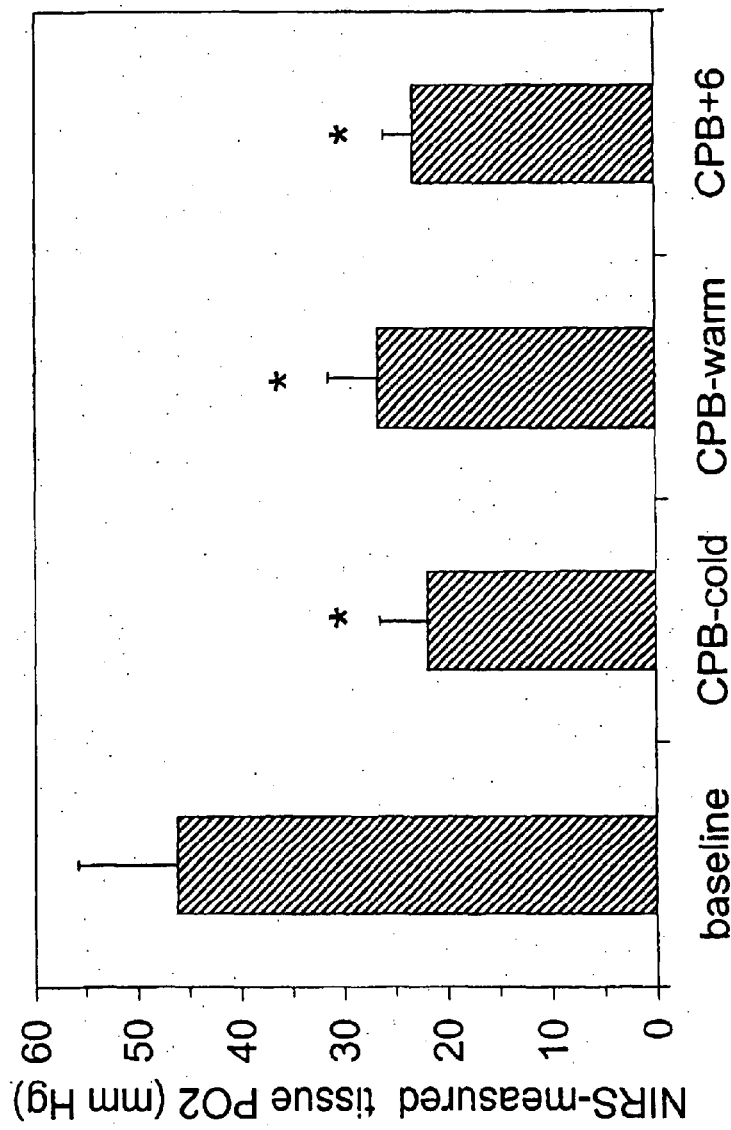
FIG. 3 is a chart showing tissue $PO_2$ during four different phases of the study as determined by the method of the present invention.

As indicated in Table 2 below where the results are presented for all 18 patients, NIRS $PO_2$ significantly fell 50% on initiation of CPB and remained constant throughout the bypass and monitored ICU period. NIR pH dropped during CPB, decreased significantly during rewarming and remained depressed six hours after CPB. Changes in tissue $PO_2$ are illustrated in FIG. 3, a graphical representation of the NIRS-measured tissue PO2 (mmHg) data during each of the four phases of the study. In conclusion, NIRS-measured muscle pH and $PO_2$ are sensitive to changes in tissue perfusion during cardiopulmonary bypass. Thus, the calibration or "virtual" model of tissue $PO_2$ is shown as accurately predicting the values measured by conventional invasive probe technology and optical measurement is sensitive enough to detect minor variations in blood flow resulting from alterations in blood pressure, temperature and metabolic demands.

TABLE 2

NIRS Parameters and CPB-Induced Variables (N = 18, mean ± sem)

|  | Baseline | CPB-Cold | CPB-Warm | CPB + 6 |
|---|---|---|---|---|
| NIRS Tissue $PO_2$ | 46 ± 10 | 22 ± 5* | 27 ± 5* | 23 ± 3* |
| NIRS Tissue pH | 7.36 ± 0.02 | 7.30 ± 0.02 | 7.20 ± 0.06* | 7.25 ± 0.02 |
| Mean pressure | 83 ± 2 | 59 ± 2 | 62 ± 2 | 79 ± 2 |
| Tissue temperature | 33.3 ± 0.4 | 31.6 ± 0.4 | 34.6 ± 0.5 | 34.7 ± 0.4 |
| Blood hematocrit | 34.2 ± 1.0 | 23.2 ± 0.6 | 23.1 ± 0.6 | 27.2 ± 0.6 |

*p < 0.05 compared to baseline

The present invention provides a method for calculating tissue $PO_2$ from reflectance spectra acquired from the surface of the tissue of interest. It has previously been shown that tissue reflectance spectra contain features related to venous oxygen saturation (Cingo et al., "Multivariate Calibration Modeling of Liver Oxygen Saturation Using Near Infrared Spectroscopy," Proc SPIE, 3911:230–236, (2000) and Soller et al., "Simultaneous measurement of hepatic tissue pH, venous oxygen saturation and hemoglobin by near infrared spectroscopy," Shock, 15:106–111, (2001)). Venous oxygen saturation is typically 70–80%, falling to 10–15% during shock. In this range, there is a linear correlation between oxygen saturation and oxygen partial pressure ($PO_2$). The Example above used a reference measurement which measures $PO_2$ in the interstitial fluid to relate near infrared (and visible) spectra to tissue $PO_2$ by applying a multivariate calibration technique, e.g., partial least squares regression. By collecting a great number of data points as multiple parameters vary the virtual model so produced is accurate and robust, so that it may subsequently be applied to determine tissue $PO_2$ from tissue reflectance spectra alone.

In general, the spectral illumination and collection steps may be carried out with any suitable spectrographic instrument. Thus, a single, broadband source may be scanned or dispersed to produce a time-sweep through the spectral band to illuminate the tissue of interest and collect reflected light, or the instrument may employ an array of different light sources for delivering radiation to the sample, e.g., between about two and about twenty light sources, each of which delivers radiation at a unique range of optical wavelengths. Each of these may be actuated in a distinctive time period, or modulated at a frequency, with corresponding synchronous collection or collection and demodulation, so that the spectral signals may be collected substantially continuously or simultaneously to effect speedy data collection.

Figure 4:
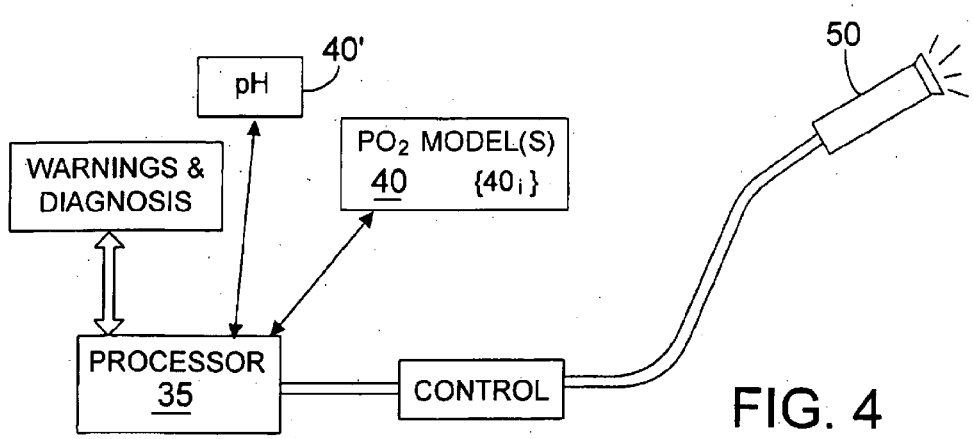
FIG. 4 shows a measurement system in accordance with the present invention.

As generally illustrated in FIG. 4, a system 30 for spectral tissue oxygen measurement includes a spectral probe 50, and a processor 35, with a virtual model 40 as discussed above stored in or accessed by the processor 35 for transforming the optical spectrum measured from a patient into a $PO_2$ value for the underlying tissue. Most preferably, the model 40 used in the analysis step is determined once and is applicable to a wide variety of patients. In this case, if the measurements are to be made through the skin, the model is preferably robust enough to account for features such as skin color, fat content, weight, etc., which may vary from one patient to the next. Alternatively, a range of models $40_i$ can be generated. In this case, during a procedure, the appropriate model $40_i$ is selected and used with a particular patient to determine the $PO_2$ of a local region of tissue. In another exemplary embodiment, the spectral variation from features such as skin color, fat content, etc, are removed as suggested in the '917 application previously cited.

In a preferred embodiment, an instrument of the invention is configured with a spectral probe 50 (e.g., either with plural discrete light sources such as LEDs that collectively span a desired band, or with a broadband source and a wavelength scanning illumination disperser or scanning detection element), and with a processor that applies the virtual spectral model or calibration equation to determine the level of tissue $PO_2$ from a non-invasively collected tissue reflectance spectrum, and the processor also determines the pH. The pH may be determined by a direct sensor measurement, but is preferably determined by the processor using a pH calibration model (indicated by 40' in FIG. 4) which may be constructed, e.g., as described in the aforesaid '403 patent. The model 40' is applied to the same or a different collected spectrum as used for the $PO_2$ determination. The instrument according to this aspect of the invention may further include diagnostic or warning determinations, which may be readily implemented in software. These may, for example combine the oxygen and pH measurements to produce a related third parameter, such as a measure of the tissue's ability to utilize available oxygen, a measure of dysoxia, or a predictive measure of tissue recovery, demise or other critical condition or endpoint. Thus, the system may detect when the $PO_2$ level has reached a critical level at which rapid change in pH will occur with potentially irreversible consequences. The system may also indicate when blood flow has been successfully restored, i.e. increases in tissue $PO_2$ levels to predetermined levels and when adequate oxygen utilization has been restored, i.e. a combined increase in $PO_2$ and pH to satisfactory levels. For instance, calculated $PO_2$ and pH values can be compared to predetermined or known $PO_2$ and pH values to assess the success or failure of a resuscitation attempt on a patient. It may further apply different threshold determinations, e.g., for diabetic and non-diabetic patients, in issuing warning indications.

The invention being thus described, various modifications and variations will occur to those of ordinary skill in the art, and all such variations are considered to be within the spirit and scope of the invention, as defined herein and in the claims appended hereto and their equivalents.

What is claimed is:

1. A non-invasive method for determining the localized tissue $PO_2$ of a sample tissue of a patient, comprising:

irradiating the sample tissue with optical radiation such that the radiation propagates into the tissue to illuminate the sample tissue;

collecting light radiation emitted from the sample tissue, the light radiation having been reflected or transmitted from the tissue;

forming an optical reflectance spectrum of the collected light radiation; and processing the optical reflectance spectrum formed with a predetermined mathematical model of tissue $PO_2$ to determine the localized tissue $PO_2$ of the sample tissue, wherein the mathematical model relates optical spectra to known tissue $PO_2$ values in tissue.

2. The method of claim 1, wherein the predetermined mathematical model of tissue $PO_2$ is constructed prior to processing the optical reflectance spectrum.

3. The method of claim 2, wherein the predetermined mathematical model of tissue $PO_2$ is constructed by:

collecting a plurality of optical spectra from at least one representative tissue sample;

collecting a plurality of direct measurements of $PO_2$ from the same representative tissue sample over an extended range; and processing the optical spectra and $PO_2$ measurements with a mathematical multivariate calibration algorithm to determine the relationship between the optical spectra and the tissue $PO_2$ measurements.

4. The method of claim 3, wherein the algorithm is a partial least-squares fitting algorithm.

5. The method of claim 3, wherein the relationship between the optical spectra and the tissue $PO_2$ measurements is linear.

6. The method of claim 3, wherein the relationship between optical spectra and the tissue $PO_2$ measurements is non-linear.

7. The method of claim 3, further comprising collecting a tissue value over an extended range of at least one parameter selected from the group consisting of temperature and pH, prior to processing the optical spectra and $PO_2$ measurements.

8. The method of claim 3, wherein the plurality of optical spectra are collected from the at least one representative tissue sample in vitro.

9. The method of claim 1, further comprising determining tissue pH simultaneously from the optical reflectance spectrum.

10. The method of claim 9, further comprising detecting a dysoxic tissue state.

11. The method of claim 9, further comprising determining a level of ischemia of the sample tissue using both the calculated pH and localized tissue $PO_2$ data.

12. The method of claim 9, further comprising determining the success or failure of a resuscitation by comparing the calculated pH and localized tissue $PO_2$ data to predetermined values for pH and tissue $PO_2$.

13. The method of claim 1, wherein the sample tissue comprises muscle or organ.

14. The method of claim 1, wherein the sample tissue is disposed underneath a covering tissue of the patient.

15. The method of claim 14, wherein irradiating comprises irradiating the sample tissue with optical radiation not substantially absorbed by the covering tissue such that the radiation propagates through the covering tissue to irradiate the sample tissue; and collecting comprises collecting radiation from the sample tissue which passes through the covering tissue to form the optical reflectance spectrum.

16. The method of claim 14, wherein the covering tissue is skin.

17. The method of claim 1, wherein the optical radiation has a wavelength between about 400 nm and 2500 nm.

18. The method of claim 1, wherein the optical radiation is near infrared radiation.

19. The method of claim 18, wherein the infrared radiation has a wavelength between about 450 nm and 1100 nm.

20. The method of claim 1, wherein the localized tissue $PO_2$ is in a $PO_2$ range of about 0.0 to about 150 mmHg.

21. The method of claim 1, wherein the sample tissue is accessed with an endoscope.

22. A device for determining the $PO_2$ of an in vivo tissue sample, comprising:

a spectrometer for irradiating the tissue sample with optical radiation spanning a range of visible and near infrared (NIR)wavelengths, and for collecting a spectrum of light returned from the tissue sample, the spectrometer forming a spectral representation thereof; and a microprocessor operative on the spectral representation to calculate the tissue $PO_2$ of the sample, the microprocessor being programmed to compare the spectral representation to a predetermined mathematical model of tissue $PO_2$ to determine the $PO_2$ of the sample.

23. The device of claim 22, wherein the spectrometer emits visible wavelengths above 400 nm.

24. The device of claim 22, wherein the predetermined mathematical model of tissue $PO_2$ relates a spectral representation of a representative tissue to tissue $PO_2$.

* * * * *